US011737915B2

(12) United States Patent
Nsofor

(10) Patent No.: US 11,737,915 B2
(45) Date of Patent: Aug. 29, 2023

(54) FUNGAL INFECTION TREATMENT

(71) Applicant: Ebelechukwu Nsofor, Los Angeles, CA (US)

(72) Inventor: Ebelechukwu Nsofor, Los Angeles, CA (US)

( * ) Notice: Subject to any disclaimer, the term of this patent is extended or adjusted under 35 U.S.C. 154(b) by 402 days.

(21) Appl. No.: 17/189,475

(22) Filed: Mar. 2, 2021

(65) Prior Publication Data
US 2022/0280335 A1   Sep. 8, 2022

(51) Int. Cl.
  A61F 7/02    (2006.01)
  B65D 81/38   (2006.01)
  B65D 25/00   (2006.01)
  A61F 7/00    (2006.01)

(52) U.S. Cl.
  CPC .............. *A61F 7/02* (2013.01); *B65D 25/00* (2013.01); *B65D 81/3876* (2013.01); *A61F 2007/0045* (2013.01)

(58) Field of Classification Search
  CPC ...... A61F 2007/0045; A61F 2007/0046; A61F 2007/0225; A61F 2007/0228; A61F 2007/0242; A61F 2007/0249; A61F 2007/0279; A61F 7/02; A61F 7/08; B65D 25/00; B65D 81/3876; F02D 2041/1432; F02D 41/1456; F02D 41/1495; F02D 41/222; Y02T 10/40
  See application file for complete search history.

(56) References Cited

U.S. PATENT DOCUMENTS

| 8,814,922 | B2 | 8/2014 | Hennings | |
|---|---|---|---|---|
| 10,155,946 | B2 | 12/2018 | Yehl | |
| 2009/0012515 | A1* | 1/2009 | Hoenig | A61B 18/203 604/20 |
| 2009/0048590 | A1 | 2/2009 | Conrad | |
| 2010/0021530 | A1* | 1/2010 | Weinfield | A61M 37/00 514/345 |
| 2010/0256551 | A1 | 10/2010 | Maltezos | |
| 2013/0041308 | A1 | 2/2013 | Hennings | |
| 2016/0157934 | A1 | 6/2016 | Kim | |
| 2016/0175612 | A1 | 6/2016 | Kazic | |
| 2019/0054309 | A1* | 2/2019 | Van Der Weide | A61N 5/025 |

FOREIGN PATENT DOCUMENTS

WO   WO2009023812   2/2009

* cited by examiner

*Primary Examiner* — Tigist S Demie

(57) ABSTRACT

A fungal infection treatment includes a container comprised of a thermally conductive material. In this way the container can be heated by the boiled water when the boiled water is poured from the cup into the container. A cover is positionable on the container to close the container to inhibit the boiled water from being spilled from the container. A drape is provided that has an opening extending therethrough. In this way the drape can be positioned on a respective one of the user's appendages having the opening exposing a nail on the respective appendage. The container is positionable in the opening when the drape is positioned on the appendage. In this way the container can transfer heat from the boiled water to the nail on the respective appendage for treating a fungal infection of the nail bed.

6 Claims, 4 Drawing Sheets

```
┌─────────────────────────────────────────┐
│ User boils water in kettle on stove or  │
│ in glass cup in microwave.              │
└─────────────────────────────────────────┘
                    │
┌─────────────────────────────────────────┐
│ User pours boiling water into aluminum  │
│ cup and covers it.                      │
└─────────────────────────────────────────┘
                    │
┌─────────────────────────────────────────┐
│ User uses drape to cover skin around    │
│ the nail bed, leaving nail bed exposed. │
└─────────────────────────────────────────┘
                    │
┌─────────────────────────────────────────┐
│ User places the bottom edge of the      │
│ aluminum cup with boiled water inside   │
│ on the nail bed for 3-4 minutes.        │
└─────────────────────────────────────────┘
                    │
┌─────────────────────────────────────────┐
│ User removes aluminum cup and drape     │
│ from toe.                               │
└─────────────────────────────────────────┘
```

FIG. 4

FUNGAL INFECTION TREATMENT

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to infection treatment device and more particularly pertains to a new infection treatment device for treating a fungal infection in a nail bed. The device includes a drape which has an opening therein which can be positioned on an appendage having a nail on the appendage being exposed in the opening. The device includes a container that is comprised of a thermally conductive material. The container is filled with boiled water and the container is positioned in the opening such that the container transfers heat from the boiled water into the nail. In this way the heat kills a fungal infection beneath the nail.

(2) Description of Related Art Including Information Disclosed Under 37 CFR 1.97 and 1.98

The prior art relates to infection treatment device including a variety of laser treatment devices for directing laser energy onto a nail bed for treating a fungal infection. The prior art also discloses a device that includes a flap that rests on a nail and which heats the nail for treating a fungal infection. The prior art discloses a variety of devices that produces heat, via an exothermic chemical reaction, for treating a fungal infection in a nail bed. In no instance does the prior art disclose a container for containing boiled water and drape that facilitates the container to be positioned on an exposed nail on an appendage for treating a fungal infection in the nail.

BRIEF SUMMARY OF THE INVENTION

An embodiment of the disclosure meets the needs presented above by generally comprising a container comprised of a thermally conductive material. In this way the container can be heated by the boiled water when the boiled water is poured from the cup into the container. A cover is positionable on the container to close the container to inhibit the boiled water from being spilled from the container. A drape is provided that has an opening extending therethrough. In this way the drape can be positioned on a respective one of the user's appendages having the opening exposing a nail on the respective appendage. The container is positionable in the opening when the drape is positioned on the appendage. In this way the container can transfer heat from the boiled water to the nail on the respective appendage for treating a fungal infection of the nail bed.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein:

FIG. 4 is a logic tree view of an embodiment of the disclosure.

DETAILED DESCRIPTION OF THE INVENTION

Figure 1:
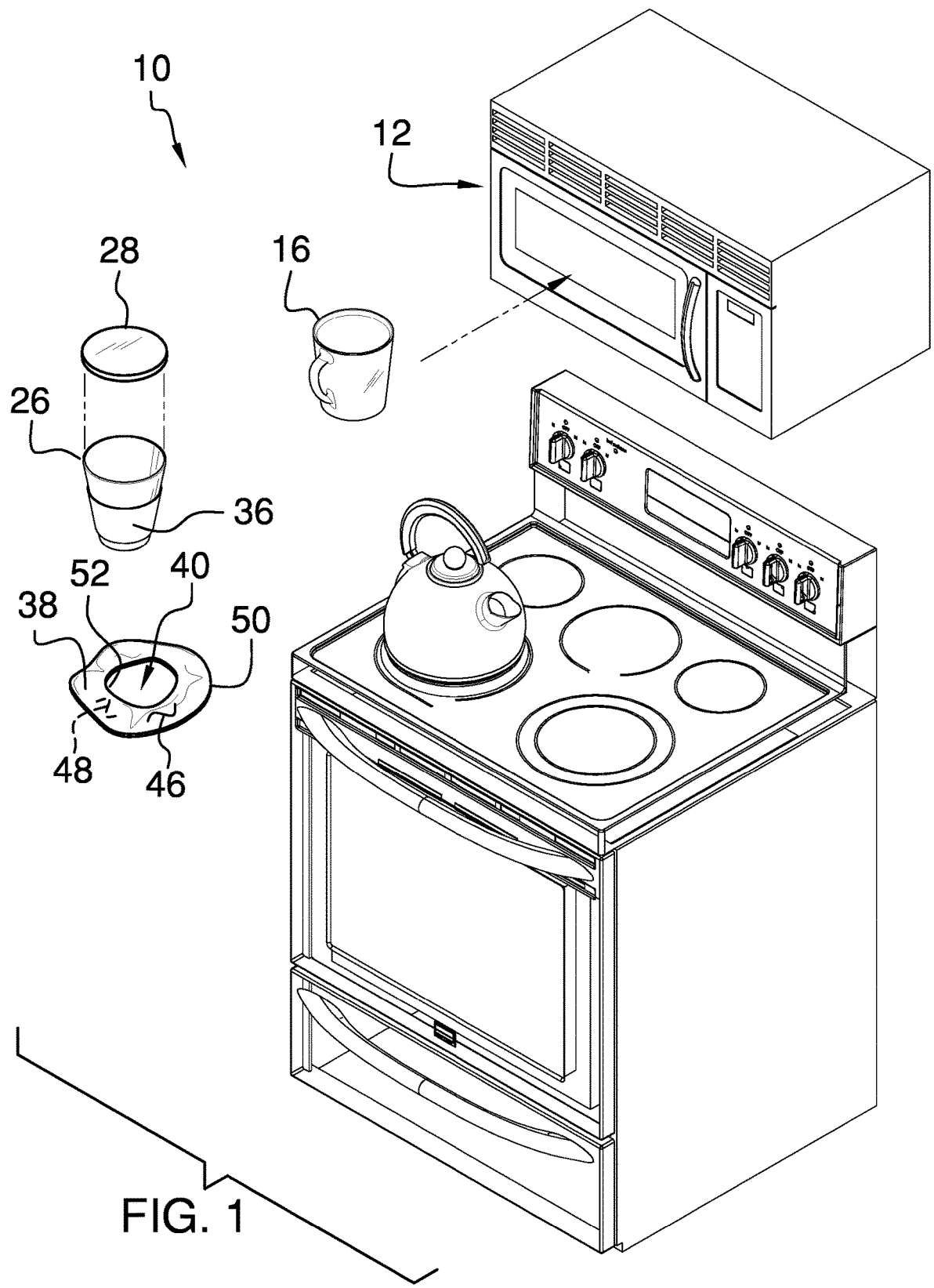
FIG. 1 is a perspective view of a fungal infection treatment according to an embodiment of the disclosure.
Figure 2:
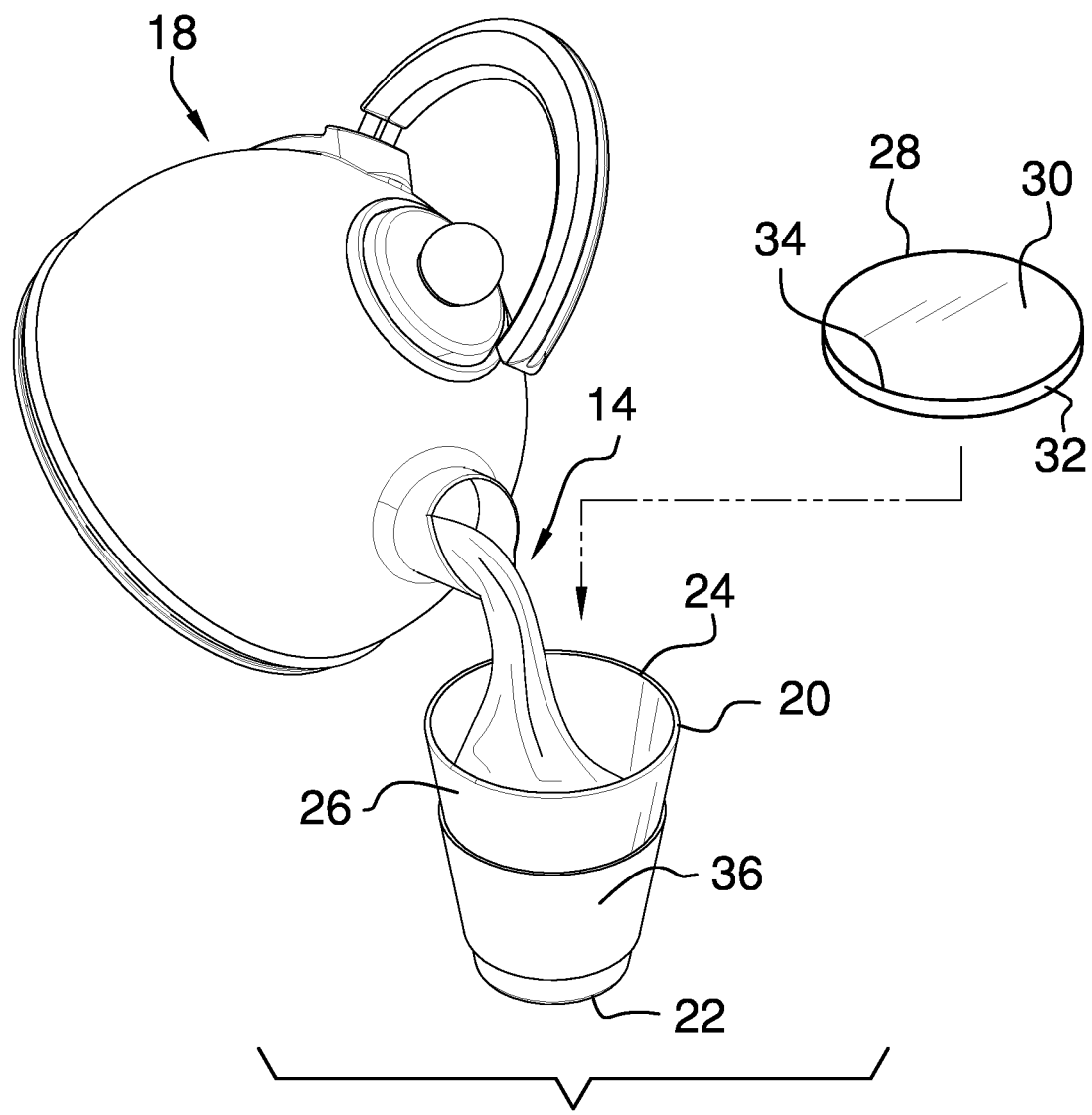
FIG. 2 is a perspective in-use view of an embodiment of the disclosure showing boiled water being poured from a tea kettle into a container.
Figure 3:
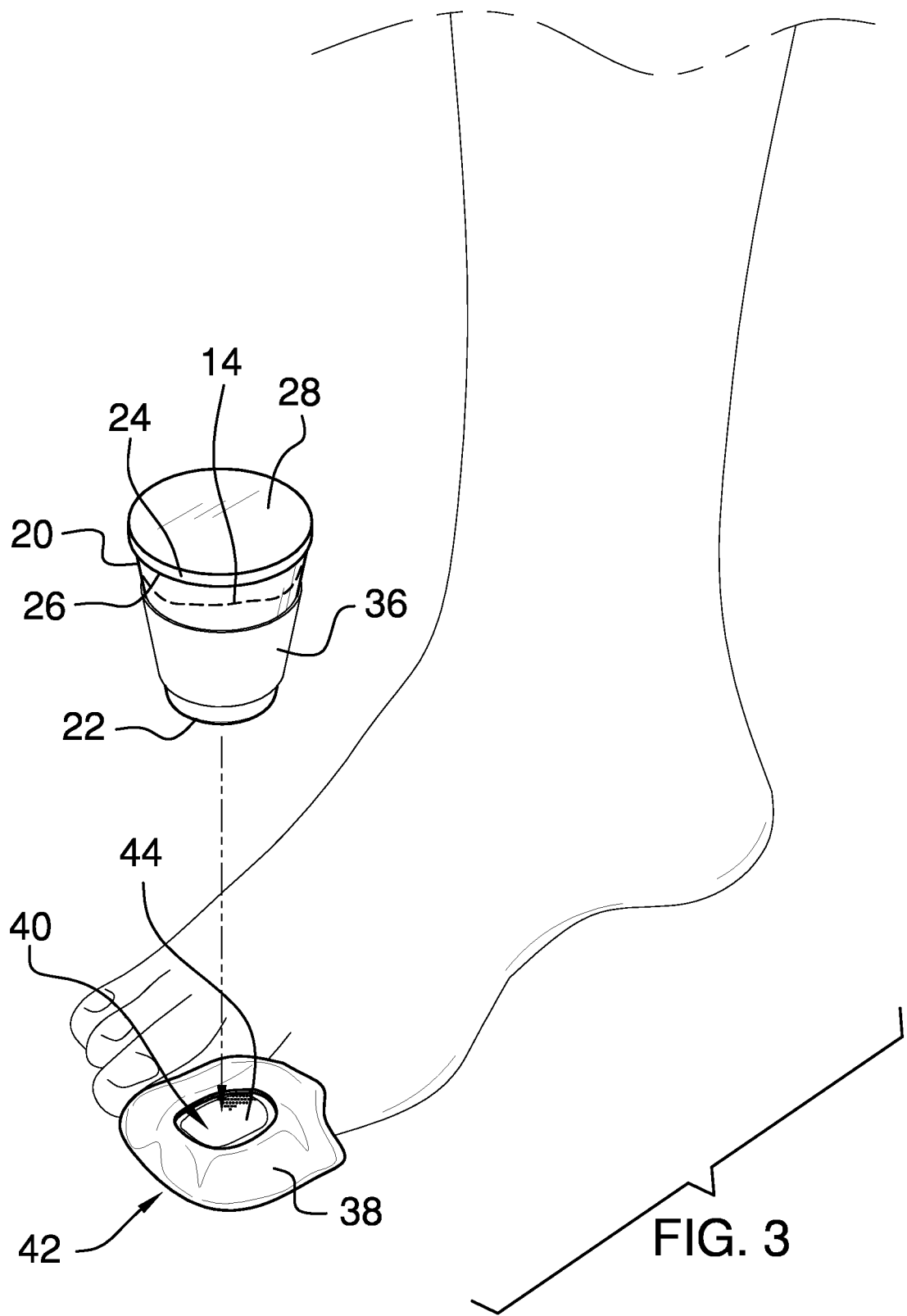
FIG. 3 is a perspective in-use view of an embodiment of the disclosure showing a container being positioned in an opening in a drape for treating a fungal infection in a nail bed.

With reference now to the drawings, and in particular to FIGS. 1 through 4 thereof, a new infection treatment device embodying the principles and concepts of an embodiment of the disclosure and generally designated by the reference numeral 10 will be described.

As best illustrated in FIGS. 1 through 4, the fungal infection treatment 10 generally comprises a cooking oven 12 has an operational temperature of at least 212.0 degrees Fahrenheit such that the cooking oven 12 can boil water 14. The cooking oven 12 may be a kitchen appliance, such as a microwave oven, a convection oven, a stove top, or any other type of cooking appliance that would commonly be found in a home. A cup 16 is included that is comprised of a heat resistant material such that the cup 16 can be heated in the cooking oven 12 without being damaged. In this way the cup 16 can be filled with water 14 that has been boiled in the cooking oven 12.

A container 20 is included that is comprised of a thermally conductive material, such as aluminum, steel or other type of rigid material that is thermally conductive. In this way the container 20 can be heated by the boiled water 14 when the boiled water 14 is poured from the cup 16 into the container 20. The container 20 has a bottom end 22, a top end 24 and an outer wall 26 extending therebetween. The top end 24 is open for having the boiled water 14 poured therethrough, and the bottom end 22 has a circular perimeter. Additionally, the container 20 may have a fluid capacity of at least 8.0 fluid ounces. As is most clearly shown in FIG. 2, the cup 16 might be filled with the boiled water 14 from a tea kettle 18 that has been heated on a stove top, rather than having the cup 16 being heated in the cooking oven 12.

A cover 28 is provided and the cover 28 is positionable on the container 20 to close the container 20. In this way the cover 28 inhibits the boiled water 14 from being spilled from the container 20. The cover 28 is comprised of a thermally insulating material to inhibit transferring heat from the boiling water 14. The thermally insulating material may comprise rubber, silicone or other type of flexible material that has thermal insulating properties. The cover 28 has a top wall 30 and a lip 32 extending downwardly from a perimeter 34 of the top wall 30. The top wall 30 rests on the top end 24 of the container 20 having the lip 32 abutting the outer wall 26 of the container 20 when the cover 28 is positioned on the container 20.

A sleeve 36 is provided and the sleeve 36 is positionable around the container 20 such that the sleeve 36 can be gripped by a user. The sleeve 36 is comprised of a thermally insulating material to inhibit the user from being burned by the container 20 when the container 20 is heated by the boiled water 14. The thermally insulating material of which the sleeve 36 is comprised may comprise rubber, silicone or other flexible material that has thermal insulating properties. The sleeve 36 extends around the outer wall 26 of the container 20 at a point located between the top end 24 and the bottom end 22.

A drape 38 is included that has an opening 40 extending therethrough such that the drape 38 can be positioned on a respective one of the user's appendages 42 having the opening 40 exposing a nail 44 on the respective appendage 42. The container 20 is positionable in the opening 40 when the drape 38 is positioned on the appendage 42. In this way the container 20 can transfer heat from the boiled water 14 to the nail 44 on the respective appendage 42 for treating a fungal infection of the nail bed. The appendage 42 may be one of the user's toes and the nail 44 may be one of the user's toe nails.

The drape 38 has a top surface 46, a bottom surface 48 and a perimeter edge 50, and the perimeter edge 50 is continuously arcuate about a center point of the drape 38 such that the drape 38 has a circular shape. The opening 40 extends through the top surface 46 and the bottom surface 48. The opening 40 is centrally positioned on the drape 38. the opening 40 has a bounding edge 52. The bounding edge 52 is continuously arcuate about a center of the opening 40 such that the opening 40 has a circular shape. the opening 40 has a diameter sufficient to accommodate the bottom end 22 of the container 20 such that the bounding edge 52 of the opening 40 abuts the outer wall 26 of the container 20.

In use, the water 14 is boiled and subsequently poured into the container 20. The cover 28 is positioned on the container 20 to contain the boiled water 14 and the drape 38 is positioned on the respective appendage 42 that has a fungal infection beneath the nail 44. Additionally, the drape 38 is oriented such that the opening 40 in the drape 38 is aligned with and exposes the nail 44 on the appendage 42. The container 20 is positioned such that the bottom end 22 of the container 20 rests on the nail 44 that is exposed by the opening 40 in the drape 38. In this way the bottom end 22 of the container 20 transfers heat from the boiling water 14 into the nail 44. Thus, the heat transferred into the nail 44 can kill a fungal infection beneath the nail 44. In this way a fungal infection that has been resistant to pharmaceutical treatments can be eliminated.

With respect to the above description then, it is to be realized that the optimum dimensional relationships for the parts of an embodiment enabled by the disclosure, to include variations in size, materials, shape, form, function and manner of operation, system and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A fungal infection treatment system for treating a fungal infection of a nail bed on a user, said system comprising:

a cooking oven having an operational temperature being at least 212.0 degrees Fahrenheit, wherein said cooking oven is configured to boil water;

a cup being comprised of a heat resistant material such that said cup can be heated in said cooking oven without being damage, wherein said cup is configured to be filled with water to be boiled in said cooking oven;

a container being comprised of a thermally conductive material, wherein said container is configured to be heated by the boiled water when the boiled water is poured from said cup into said container;

a cover being positionable on said container to close said container, wherein said cover is configured to inhibit the boiled water from being spilled from said container, said cover being comprised of a thermally insulating material, wherein said cover is configured to inhibit transferring heat from the boiling water;

a sleeve being positionable around said container, wherein said sleeve is configured to be gripped by a user, said sleeve being comprised of a thermally insulating material, wherein said sleeve is configured to inhibit the user from being burned by said container when said container is heated by the boiled water; and a drape having an opening extending therethrough, wherein said drape is configured to be positioned on a respective one of the user's appendages having said opening exposing a nail on the respective appendage, said container being positionable in said opening when said drape is positioned on the appendage, wherein said container is configured to transfer heat from the boiled water to the nail on the respective appendage for treating a fungal infection of the nail bed.

2. The system according to claim 1, wherein:
said container has a bottom end, a top end and an outer wall extending therebetween, said top end being open, wherein said container is configured to have the boiled water poured therethrough; and
said opening in said drape has a diameter being sufficient to accommodate said bottom end of said container.

3. The assembly according to claim 1, wherein:
said container has a bottom end, said bottom end having a circular perimeter; and
said drape has a top surface, a bottom surface and a perimeter edge, said perimeter edge being continuously arcuate about a center point of said drape such that said drape has a circular shape, said opening extending through said top surface and said bottom surface, said opening being centrally positioned on said drape, said opening having a bounding edge, said bounding edge being continuously arcuate about a center of said opening such that said opening has a circular shape thereby facilitating said opening to conform to the shape of said bottom end of said container.

4. The assembly according to claim 3, wherein said opening has a diameter sufficient to accommodate said bottom end of said container such that said bounding edge of said opening abuts said outer wall of said container.

5. A fungal infection treatment system for treating a fungal infection of a nail bed on a user, said system comprising:
a cooking oven having an operational temperature being at least 212.0 degrees Fahrenheit, wherein said cooking oven is configured to boil water;
a cup being comprised of a heat resistant material such that said cup can be heated in said cooking oven without being damaged, wherein said cup is configured to be filled with water to be boiled in said cooking oven;
a container being comprised of a thermally conductive material, wherein said container is configured to be heated by the boiled water when the boiled water is poured from said cup into said container, said container having a bottom end, a top end and an outer wall extending therebetween, said top end being open, wherein said container is configured to have the boiled water poured therethrough, said bottom end having a circular perimeter;
a cover being positionable on said container to close said container, wherein said cover is configured to inhibit the boiled water from being spilled from said container, said cover being comprised of a thermally insulating material, wherein said cover is configured to inhibit transferring heat from the boiling water, said cover having a top wall and a lip extending downwardly from a perimeter of said top wall, said top wall resting on said top end of said container having said lip abutting said outer wall of said container when said cover is positioned on said container;
a sleeve being positionable around said container, wherein said sleeve is configured to be gripped by a user, said sleeve being comprised of a thermally insulating material, wherein said sleeve is configured to inhibit the user from being burned by said container when said container is heated by the boiled water, said sleeve extending around said outer wall of said container at a point being located between said top end and said bottom end; and
a drape having an opening extending therethrough, wherein said drape is configured to be positioned on a respective one of the user's appendages having said opening exposing a nail on the respective appendage, said container being positionable in said opening when said drape is positioned on the appendage, wherein said container is configured to transfer heat from the boiled water to the nail on the respective appendage for treating a fungal infection of the nail bed, said drape having a top surface, a bottom surface and a perimeter edge, said perimeter edge being continuously arcuate about a center point of said drape such that said drape has a circular shape, said opening extending through said top surface and said bottom surface, said opening being centrally positioned on said drape, said opening having a bounding edge, said bounding edge being continuously arcuate about a center of said opening such that said opening has a circular shape, said opening having a diameter sufficient to accommodate said bottom end of said container such that said bounding edge of said opening abuts said outer wall of said container.

6. A fungal infection treatment system for treating a fungal infection of a nail bed on a user, said system comprising:
a container being comprised of a thermally conductive material, wherein said container is configured to be heated by boiled water when the boiled water is poured into said container, said container having a bottom end, a top end and an outer wall extending therebetween, said top end being open, wherein said container is configured to have the boiled water poured therethrough, said bottom end having a circular perimeter;
a cover being positionable on said container to close said container, wherein said cover is configured to inhibit the boiled water from being spilled from said container, said cover being comprised of a thermally insulating material, wherein said cover is configured to inhibit transferring heat from the boiling water, said cover having a top wall and a lip extending downwardly from a perimeter of said top wall, said top wall resting on said top end of said container having said lip abutting said outer wall of said container when said cover is positioned on said container;
a sleeve being positionable around said container, wherein said sleeve is configured to be gripped by a user, said sleeve being comprised of a thermally insulating material, wherein said sleeve is configured to inhibit the user from being burned by said container when said container is heated by the boiled water, said sleeve extending around said outer wall of said container at a point being located between said top end and said bottom end; and
a drape having an opening extending therethrough, wherein said drape is configured to be positioned on a respective one of the user's appendages having said opening exposing a nail on the respective appendage, said container being positionable in said opening when said drape is positioned on the appendage, wherein said container is configured to transfer heat from the boiled water to the nail on the respective appendage for treating a fungal infection of the nail bed, said drape having a top surface, a bottom surface and a perimeter edge, said perimeter edge being continuously arcuate about a center point of said drape such that said drape has a circular shape, said opening extending through said top surface and said bottom surface, said opening being centrally positioned on said drape, said opening having a bounding edge, said bounding edge being continuously arcuate about a center of said opening such that said opening has a circular shape, said opening having a diameter sufficient to accommodate said bottom end of said container such that said bounding edge of said opening abuts said outer wall of said container.

* * * * *